United States Patent [19]

Iwai et al.

[11] Patent Number: 4,916,130

[45] Date of Patent: Apr. 10, 1990

[54] PLATELET AGGLUTINATION-INHIBITING AGENT

[75] Inventors: Masakazu Iwai; Chikara Fukaya; Kazumasa Yokoyama, all of Osaka, Japan

[73] Assignee: Green Cross Corporation, Osaka, Japan

[21] Appl. No.: 241,447

[22] Filed: Sep. 8, 1988

[30] Foreign Application Priority Data

Sep. 8, 1987 [JP] Japan .................. 62-224442

[51] Int. Cl.$^4$ .................. A61K 31/535; A61K 31/16; A61K 31/415

[52] U.S. Cl. .................. 514/237.8; 514/399; 514/400; 514/428; 514/315; 514/547; 514/528; 514/578; 514/562; 514/627; 514/616; 514/550

[58] Field of Search .............. 514/616, 627, 562, 578, 514/528, 547, 550, 315, 237.8, 399, 400, 428

[56] References Cited

FOREIGN PATENT DOCUMENTS 0195433 9/1986 European Pat. Off. .

*Primary Examiner*—Frederick E. Waddell
*Attorney, Agent, or Firm*—Sughrue, Mion, Zinn, Macpeak & Seas

[57] ABSTRACT

An antithrombotic composition containing an amide derivative which is obtained by binding a sulfur-containing amine to an unsaturated fatty acid having 4 to 13 carbon atoms through an amide bond and which exerts a high platelet agglutination-inhibiting effect.

4 Claims, No Drawings

PLATELET AGGLUTINATION-INHIBITING AGENT

FIELD OF THE INVENTION

The present invention is directed towards a composition for inhibiting the agglutination of platelets which comprises an amide derivative consisting of a sulfur-containing amine and an unsaturated fatty acid, as active ingredients, and a pharmaceutically acceptable carrier.

BACKGROUND OF THE INVENTION

JP-A-62-57 (term "JP-A" as used herein means an "unexamined published Japanese patent application") corresponding to U.S. Pat. Ser. No. 841,417, EP-A-0 195 433 both report that novel amide derivatives, obtained by binding a sulfur-containing amine to an unsaturated fatty acid having 5 to 18 carbon atoms through an amide bond, provide a peptic ulcer-preventative effect as well as an anti-inflammatory effect.

SUMMARY OF THE INVENTION

We have studied the pharmacological effects of the above-mentioned amide derivatives and surprisingly have found that these amide derivatives possess platelet agglutination-inhibiting properties. Further, we have found that specific compounds among these amide derivatives exhibit a particularly high platelet agglutination-inhibiting effect.

Accordingly, it is an object of the present invention to provide a compound having a platelet agglutination-inhibiting effect.

The present invention provides a composition for inhibiting the agglutination of platelets comprising an amide derivative which is obtained by binding a sulfur-containing amine, i.e., an amino compound having sulfur atom(s) to an unsaturated fatty acid having 4 to 13 carbon atoms through an amide bond, as an active ingredient, and a pharmaceutically acceptable carrier.

DETAILED DESCRIPTION OF THE INVENTION

The amide derivatives of the present invention are prepared by binding an amino group of an sulfur-containing amine to a carboxy group of an unsaturated fatty acid through an amide bond. If the amide derivatives contain an SH group, a compound in which the SH group is alkylated is also included in the amide derivatives to be used herein. Unless otherwise noted, the expression "amide derivative" used herein includes these alkylated compounds. Further, the alkyl group in the alkylated compound may be substituted. Examples of the alkyl group include (1) a lower alkyl group such as methyl, ethyl, n-propyl, n-butyl; (2) an N,N-di-lower alkylcarbamide-lower alkyl group such as N,N-dimethyl-carbamide-methyl, N,N-diethyl-carbamide-methyl; (3) a lower-alkoxycarbonyl-lower alkyl group such as ethoxycarbonylmethl, ethoxycarbonylethyl; (4) a carboxy-lower alkyl group such as carboxymethyl, carboxymethyl; (5) a cyano-lower alkyl group such as cyanomethyl; (6) a β-amino-lower alkyl group such as —CH$_2$CH$_2$NH$_2$; (7) a benzoyl-lower alkyl group such as —CH$_2$COC$_6$H$_5$; (8) a carboxamide-lower alkyl group such as —CH$_2$CONH$_2$; (9) a cycloalkyl-lower alkyl group such as cyclohexylmethyl, cyclohexylethyl; (10) an aralkyl (aryl-lower alkyl) group such as benzyl, phenylethyl; (11) an N-lower alkyl-piperidinyl-lower alkyl group such as N-methyl-2-piperidinyl-methyl; (12) a piperidinyl-lower alkyl group such as β-(1-piperidinyl)-ethyl; (13) a lower alkyl group substituted with at least one nitrogen-containing heterocyclic group(s) such as pyrrolidine, morpholine and imidazole.

The expression "lower alkyl" used herein means an alkyl group having 1 to 4 carbon atoms (C$_1$–C$_4$).

The sulfur-containing amine of the present invention is not particularly restricted so long as it is an amino compound having sulfur atom(s). It is preferable that the sulfur-containing amine includes one or two amino groups. Examples of the sulfur-containing amines include cystine, cysteine, cystamine, cysteamine, taurine, methionine, ethionine and lanthionine. Among these compounds, cystamine is particularly preferable. The sulfur-containing amine also includes those having an SH group substituted by the alkyl group(s) defined above. The sulfur atom(s) in the sulfur-containing amine may be in the form of a sulfur oxide.

The unsaturated fatty acid of the present invention is not particularly restricted so long as it has 4 to 13, preferable 5 to 8, carbon atoms. It is preferable that the unsaturated group(s) in the unsaturated fatty acid contain double bonds. It is preferable that the unsaturated fatty acid has a single unsaturated bond, though it is not restricted thereto. The position of the unsaturated bond is not particularly restricted. Examples of the unsaturated fatty acid include 2-pentenoic acid, 2-hexenoic acid, 2-heptenoic acid and 2-octenoic acid.

Among these unsaturated fatty acids, those represented by the following general formula are preferable in particular:

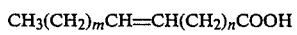

wherein m+n is an integer of 0 to 9.

In the above formula, m preferably represents an integer of 0 to 9, more preferably 1 to 4, while n preferably represents an integer of 0 or 1, more preferably 0.

Preferable examples of the amide derivatives of the present invention are those represented by formula (I)

wherein p+q is an integer of from 0 to 9; A represents an alkylene group; Y represents a sulfur atom or a sulfinyl group; and X represents a hydrogen atom, an alkyl group, a substituted alkyl group, a carbamoyl group or a group represented by the formula, CH$_3$(CH$_2$)$_p$CH=CH—(CH$_2$)$_q$CONH—A—Y—, wherein p, q, A and Y are defined as above.

In formula (I), p+q is an integer of 0 to 9, preferably 1 to 4. p is an integer of 0 to 9, preferably 1 to 4, while q is preferably 0. Preferably, alkylene group A contains 1 to 3 carbon atoms and is straight-chain or branched, i.e., methylene and ethylene. An ethylene group is particularly preferable.

X preferably represents a group represented by the formula, CH$_3$(CH$_2$)$_p$CH=CH(CH$_2$)$_q$CONH—A—Y—, wherein p, q, A and Y are defined as above.

The amide derivatives of the present invention may be prepared by any known amidation process. For example, an unsaturated fatty acid or its reactive derivative may be allowed to react with a sulfur-containing amine. Optionally, a dehydrating agent may be employed.

Examples of reactive derivatives of unsaturated fatty acids include acid halides such as acid chloride and acid bromide, active esters and acid anhydrides.

Examples of dehydrating agents include N,N'-disubstituted carbodiimides such as N,N'-dicyclohexylcarbodiimide and N,N'-carbonyldiimidazole.

The above reaction may be effected in the presence of an inert solvent such as ethyl acetate, chloroform or ether. The reaction may be carried out at 0° to 50° C. for 30 minutes to 4 hours.

The unsaturated fatty acid may be employed in an amount of 1 to 3 mols per mol of the sulfur-containing amine. The dehydrating agent may be preferably added in an amount of 1 to 3 mols per mol of the sulfur-containing amine.

The reactive derivative of an unsaturated fatty acid such as an acid halide may be prepared by treating the unsaturated fatty acid with phosphorus trichloride, phosphorus pentachloride or, more preferably, thionyl chloride at a weight ratio of the unsaturated fatty acid to the thionyl chloride of 1/1 to 5. The reaction is preferably carried out at 40° to 80° C. for 4 to 29 hours. The acid halide thus obtained may be purified by any known process including distillation.

An amide derivative having an SH group may be alkylated to give an alkylated compound. A disulfide group (S—S) of an amide derivative may be reduced to an SH group before alkylation, to obtain an alkylated compound. The alkylation may be carried out by a known method (Chem. Pharm. Bull., 35(11), 4616 (1987)).

The amide derivatives thus obtained may be isolated and purified by conventional methods, including solution inversion, recrystallization or chromatography.

The amide derivatives used in the present invention exert high platelet agglutination-inhibiting effects on mammals including man, horses, dogs, mice and rats. Therefore, these compounds are highly useful as antithrombotic compounds, in particular, for the treatment of thrombotic diseases including thrombosis, cerebral infarction and myocardial infarction.

The antithrombotic compounds of the present invention together with known pharmaceutically acceptable carriers, may be formulated into antithrombotic pharmaceutical compositions. These compositions may be orally or parenterally administered in antithrombotic effective amounts. Any conventional mode of administration is contemplated. Modes of administration include, but are not limited to, subcutaneous, intramuscular, or intervenous injection, oral administration, administration by intervenous drip or rectal infusion.

These compositions may be in any conventional form, including capsules, tablets, powders, granules, syrups, suppositories and injectable solutions.

The amide derivative of the present invention may be administered to an adult in a dosage ranging from 1 to 100 mg once or several times per day. The dosage may vary depending on the age, body weight, conditions and therapeutic reactions of the patient.

The following Examples further illustrate the present invention in detail, but are not to be construed to limit the scope thereof.

TEST EXAMPLE 1

Blood was collected from the abdominal aorta of a sacrificed rat. The obtained blood was then mixed with a solution of 3.9% sodium citrate at a ratio of one part by volume of sodium citrate solution to nine parts by volume of the blood. The mixture was configured at 116×g for 10 minutes to give a platelet-rich plasma (PRP). The supernatant was further centrifuged at 1,638×g for 10 minutes to give a platelet-poor plasma (PPP). The PRP was diluted with the PPP so as to give a platelet concentration of 50 to $1 \times 10^6$ cells/μl.

The agglutination of platelets was determined with an aggligometer (RINKADENKI HUSM type). Sample solutions of 25 μl were obtained by dissolving each test compound in methanol and adding the resulting solution to a physiological saline solution so as to give a final methanol concentration of 1%. These sample solutions were then added to 225 μl of PRP preliminarily maintained at 37° C. while stirring at 800 rpm. Three minutes thereafter, 50 μl of an agglutination inducer was added thereto while continuously stirring. The results are shown in Table 1.

Collagen, when employed as the agglutination inducer, was added at a concentration of 0.14 mg/ml. The 50% inhibition concentration of each test compound was calculated from the inhibition ratio thereof for the maximum thrombotic agglutination.

Arachidonic acid, when employed as the agglutination inducer, was added at a concentration of 1 mM. The 50% effective concentration of each test compound was calculated by comparing the onset time from the addition of the arachidonic acid to the initiation of the agglutination with that of the control group.

The test compounds used are listed below.

Compound 1:
{SCH$_2$CH$_2$NH—COCH=CHCH$_2$CH$_3$]$_2$

Compound 2:
{SCH$_2$CH$_2$NH—COCH=CH(CH$_2$)$_2$CH$_3$]$_2$

Compound 3:
{SCH$_2$CH$_2$NH—COCH=CH(CH$_2$)$_3$CH$_3$]$_2$

Compound 4:
{SCH$_2$CH$_2$NH—COCH=CH(CH$_2$)$_4$CH$_3$]$_2$

TABLE 1

| | IC$_{50}$ (μM) | |
|---|---|---|
| Test Compound | Agglutination induced by collagen | Agglutination induced by arachidonic acid |
| Compound 1 | 15 | 13 |
| Compound 2 | 4 | 6.7 |
| Compound 3 | 26 | 17 |
| Compound 4 | 290 | 135 |

TEST EXAMPLE 2

An acute toxicity test was performed by orally administering compounds 1-4 to rats. Each rat received a dosage of 8 g/kg of one of the four compounds. All rats remained viable.

EXAMPLE 1

| Tablet Composition | |
|---|---|
| (1) Compound 2 | 0.5 mg |
| (2) tablet fine particles No. 209 (manufactured by Fuji Kagaku K.K., consisting of 20% of magnesium aluminate metasilicate; 30% of corn starch and 50% of lactose) | 46.6 mg |
| (3) crystalline cellulose | 24.0 mg |
| (4) carboxymethylcellulose calcium | 4.0 mg |
| (5) magnesium stearate | 0.4 mg |

The components (1), (3) and (4) were preliminarily passed through a sieve of 100 mesh. The components (1), (3), (4) and (2) were each dried to give a definite moisture content. Then, these components were mixed in a blender at a weight ratio as defined above. To the mixture thus homogenized, the component (5) was added and the resulting mixture was blended for a short period of time, i.e., 30 seconds. The obtained antithrombotic pharmaceutical composition was tableted utilizing a tablet machine provided with a pounder (6.3 mm in diameter×6.0 mm in R). The resultant tablets each weighed about 75.5 mg.

These tablets may be coated with film coatings that are soluble in the stomach. Conventional film coatings may be employed, i.e., polyvinylacetal diethylaminoacetate. Further, an edible colorant may be optionally included in the film.

EXAMPLE 2

| Capsule Composition | |
|---|---|
| (1) Compound 2 | 2.5 g |
| (2) lactose | 935 g |
| (3) magnesium stearate | 15 g |

Each component was weighed and homogeneously mixed together. 190 mg portions of the obtained powdery antithrombotic pharamaceutical composition were filled into hard gelatin capsules.

EXAMPLE 3

| Injectable solution Composition | |
|---|---|
| (1) Compound 2 | 0.5 mg |
| (2) glucose | 100 mg |
| (3) physiological saline solution | 10 ml |

The above components were mixed together and filtered through a membrane filter. The resultant filtrate was then filtered again under sterile conditions. The obtained filtrate was pipetted into vials under sterile conditions. After filling, each vial was sealed under nitrogen gas, to give an injectable solution suitable for intravenous administration.

REFERENCE EXAMPLE 1

Synthesis of Compound 2
$[SCH_2CH_2NH-COCH=CH(CH_2)_2CH_3]_2$ 15 g of 2-hexenoic acid was mixed with 20 ml of thionyl chloride and heated while stirring for 15 hours. After the completion of the reaction, the thionyl chloride was distilled off and the residue was distilled under reduced pressure to give an acid chloride. 5.0 g of cystamine and 10.1 ml of triethylamine were dissolved in 150 ml of ethylene acetate. To the solution thus obtained, 9.6 g of the acid chloride obtained above dissolved in 15 ml of ethyl acetate was added dropwise under ice-cooling. The reaction mixture was allowed to react at 0° C. for 30 minutes and then at room temperature for 15 hours. 100 ml of water was then added thereto. The reaction/water mixture was filtered. The solid matter was then dissolved in ethylacetate and recrystallized. 10.8 g of desired compound 2 was obtained (yield: 57%).

Properties of compound 2:
m.p.: 137° to 138° C.;
IR $\nu_{max}^{KBr}$ cm$^{-1}$: 3300, 3050, 2950, 2860, 1665, 1620, 1540, 1465, 975;
NMR (CDCl$_3$) δ: 0.90 (t, 6H, J=7 Hz), 2.13 (dt, 4H, J=6, 6 Hz), 2.80 (t, 4H, J=6 Hz), 3.58 (dt, 4H, J=6, 6 Hz), 5.85 (dt, 2H, J=16, 1 Hz), 6.80 (dt, 2H, J=16, 16H), 6.90 (br, 2H).

REFERENCE EXAMPLE 2

Synthesis of Compound 4
$[SCH_2CH_2NH-COCH=CH(CH_2)_4CH_3]_2$

Compound 4 was prepared in the same manner as in Reference Example 1 except that 2-octenoic acid (3.9 g, 27.6 mmol) was used in place of 2-hexenoic acid. 3.4 g of desired compound 4 was obtained (yield: 85%).

Properties of compound 4:
m.p.: 131° to 133° C.;
IR $\nu_{max}^{KBr}$ cm$^{-1}$: 3300, 3050, 2920, 2850. 1650, 1620, 1445, 970;
NMR (CDCl$_3$+CF$_3$COOH) δ ppm: 0.9 (brt, 6H), 2.15 (brt, 4H), 2.85 (t, 4H, J=7 Hz), 3.6 (t, 4H, J=7 Hz), 5.9 (dt, 2H, J=16, 1 Hz), 6.8 (dt, 2H, J=16, 7 Hz), 6.9 (br, 2H).

While the inventin has been described in detail and with reference to specific embodiments thereof, it will be apparent to one skilled in the art that various changes and modifications can be made therein without departing from the spirit and scope thereof.

What is claimed is:
1. A method of treating a patient in need of an agent inhibiting the agglutination of platelets which comprises administering thereto in an amount effective to inhibit agglutination of platelets,
an amide derivative comprising a sulfur-containing amine, selected from the group consisting of cystine, cysteine, cystamine, cysteamine, taurine, methionine, ethyonine and lantionine, or those having an SH group substituted by an alkyl group, bound, through an amide bond, to an unsaturated fatty acid having 4 to 13 carbon atoms represented by the general formula:

$$CH_3(CH_2)_mCH=CH(CH_2)_nCOOH$$

wherein m+n is an integer of from 0 to 9.

2. A method according to claim 1, wherein said sulfur-containing amine is crystamine or an alkylated cystamine.

3. A method according to claim 1, wherein said sulfur-containing amine is an alkylated sulfur-containing amine with the alkyl group being one selected from the group consisting of: C$_1$–C$_4$ alkyl; N,N-di C$_1$–C$_4$ alkyl-carbamide-C$_1$–C$_4$ alkyl; C$_1$–C$_4$ alkoxycarbonyl-C$_1$–C$_4$ alkyl; carboxy-C$_1$–C$_4$ alkyl; cyano-C$_1$–C$_4$ alkyl; β-amino-C$_1$–C$_4$ alkyl; benzoyl-C$_1$–C$_4$ alkyl; carboxamide-C$_1$–C$_4$ alkyl; cycloalkyl-C$_1$–C$_4$ alkyl; aralkyl; N-C$_1$–C$_4$ alkylpiperidinyl-C$_1$–C$_4$ alkyl; piperidinyl-C$_1$–C$_4$ alkyl; and C$_1$–C$_4$ alkyl substituted with at least one nitrogen containing heterocyclic group selected from the group consisting of pyrrolidine, morpholine and imidazole.

4. A method according to claim 1, wherein said amide derivative is:

$[SCH_2CH_2NH-COCH=CH(CH_2)_2CH_3]_2$.

* * * * *